(12) United States Patent
Yan

(10) Patent No.: US 10,139,831 B2
(45) Date of Patent: Nov. 27, 2018

(54) VEHICLE SYSTEM AND VEHICLE CONTROLLER FOR CONTROLLING VEHICLE

(71) Applicants: DENSO International America, Inc., Southfield, MI (US); DENSO CORPORATION, Kariya, Aichi-pref. (JP)

(72) Inventor: Yu Yan, Livonia, MI (US)

(73) Assignees: DENSO International America, Inc., Southfield, MI (US); DENSO CORPORATION, Kariya (JP)

(*) Notice: Subject to any disclaimer, the term of this patent is extended or adjusted under 35 U.S.C. 154(b) by 0 days.

(21) Appl. No.: 15/461,812

(22) Filed: Mar. 17, 2017

(65) Prior Publication Data

US 2018/0267557 A1    Sep. 20, 2018

(51) Int. Cl.
| | |
|---|---|
| *A61B 3/11* | (2006.01) |
| *A61B 3/14* | (2006.01) |
| *A61B 5/00* | (2006.01) |
| *A61B 5/01* | (2006.01) |
| *A61B 5/18* | (2006.01) |
| *B60R 1/00* | (2006.01) |
| *G05D 1/00* | (2006.01) |
| *G05D 1/02* | (2006.01) |

(Continued)

(52) U.S. Cl.
CPC .......... *G05D 1/0246* (2013.01); *A61B 3/112* (2013.01); *A61B 3/14* (2013.01); *A61B 5/02055* (2013.01); *A61B 5/18* (2013.01); *A61B 5/4266* (2013.01); *A61B 5/6802* (2013.01); *B60R 1/00* (2013.01); *G05D 1/0088* (2013.01); *A61B 5/01* (2013.01); *A61B 5/024* (2013.01); *B60R 2300/8006* (2013.01); *G05D 2201/0213* (2013.01)

(58) Field of Classification Search
CPC ............... G05D 1/0246; G05D 1/0088; G05D 2201/0213; A61B 5/02055; A61B 5/18; A61B 5/6802; B60R 2300/8006; B62D 15/025; B62D 15/0255
See application file for complete search history.

(56) References Cited

U.S. PATENT DOCUMENTS

| | | | | |
|---|---|---|---|---|
| 6,599,243 | B2 * | 7/2003 | Woltermann | A61B 5/165 340/425.5 |
| 2013/0226406 | A1 * | 8/2013 | Ueda | B62D 1/28 701/41 |

(Continued)

FOREIGN PATENT DOCUMENTS

| | | | |
|---|---|---|---|
| JP | 2011-39601 | * | 2/2011 |
| WO | 2015134376 A1 | | 9/2015 |

*Primary Examiner* — Michael J Zanelli

(57) ABSTRACT

A processor is coupled to a vehicle, the processor being configured to store a lane change parameter. A feature sensor detects a feature of a passenger in the vehicle. The processor is programmed to control the vehicle to execute an assisted lane change based on the lane change parameter, the lane change parameter defining a characteristic of the assisted lane change, communicate with the feature sensor to detect the feature of the passenger during the assisted lane change, determine whether the passenger was comfortable during the assisted lane change based on the detected feature of the passenger, and modify the lane change parameter upon determining that the passenger was uncomfortable.

16 Claims, 4 Drawing Sheets

(51) Int. Cl.
    *A61B 5/024*    (2006.01)
    *A61B 5/0205*   (2006.01)

(56)            References Cited

U.S. PATENT DOCUMENTS

2013/0226408 A1*  8/2013  Fung ................... B60W 40/09
                                                       701/41
2014/0309892 A1  10/2014  Ricci
2015/0158425 A1*  6/2015  Han ....................... B60O 9/00
                                                       701/41
2015/0158486 A1   6/2015  Healey et al.
2017/0370732 A1* 12/2017  Bender ................ G01C 21/34
2018/0022361 A1*  1/2018  Rao ..................... B60R 16/037

* cited by examiner

VEHICLE SYSTEM AND VEHICLE CONTROLLER FOR CONTROLLING VEHICLE

TECHNICAL FIELD

The present disclosure relates to a vehicle system and a vehicle controller for controlling a vehicle.

BACKGROUND

In recent times, assisted driving and automatic driving have emerged as trending technologies. As one example of such technologies, a vehicle controller may perform an assisted lane change or an automatic lane change by controlling the steering system of a vehicle. However, there is a concern that with such technologies, the assisted or automatic lane change may not sufficiently account for the comfort of a passenger.

SUMMARY

According to one aspect of the present disclosure, a processor is coupled to a vehicle, the processor being configured to store a lane change parameter. A feature sensor detects a feature of a passenger in the vehicle. The processor is programmed to control the vehicle to execute an assisted lane change based on the lane change parameter, the lane change parameter defining a characteristic of the assisted lane change, communicate with the feature sensor to detect the feature of the passenger during the assisted lane change, determine whether the passenger was comfortable during the assisted lane change based on the detected feature of the passenger, and modify the lane change parameter upon determining that the passenger was uncomfortable.

According to a second aspect of the present disclosure, a central processing unit (CPU) is coupled to a vehicle and is in communication with a feature sensor that detects a feature of a passenger in the vehicle. A memory is coupled to the CPU, the memory being configured to store a lane change parameter. The CPU is programmed to communicate with the feature sensor to detect the feature of the passenger during an assisted lane change, the lane change parameter defining a characteristic of the assisted lane change, determine whether the passenger was comfortable during the assisted lane change based on the detected feature of the passenger, and modify the lane change parameter upon determining that the passenger was uncomfortable.

Still other objects, advantages, and features of the present disclosure will become apparent after considering the detailed description and drawings.

DETAILED DESCRIPTION

First Embodiment

A first embodiment of the present disclosure will be explained with reference to FIGS. 1 to 3.

Figure 1:
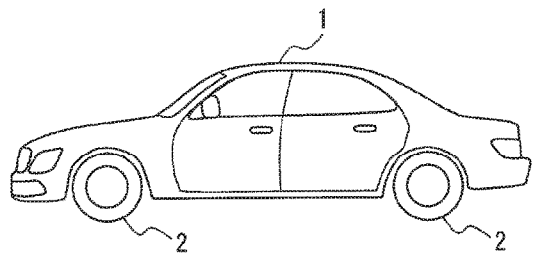
FIG. 1 is an overview of a vehicle.

FIG. 1 shows a subject vehicle 1 including a plurality of wheels 2. While FIG. 1 shows a sedan type passenger vehicle, this is not intended to be limiting. The present disclosure is equally applicable to all types of road vehicles, including trucks, busses, as well as specialized vehicles such as agricultural machinery.

Figure 2:
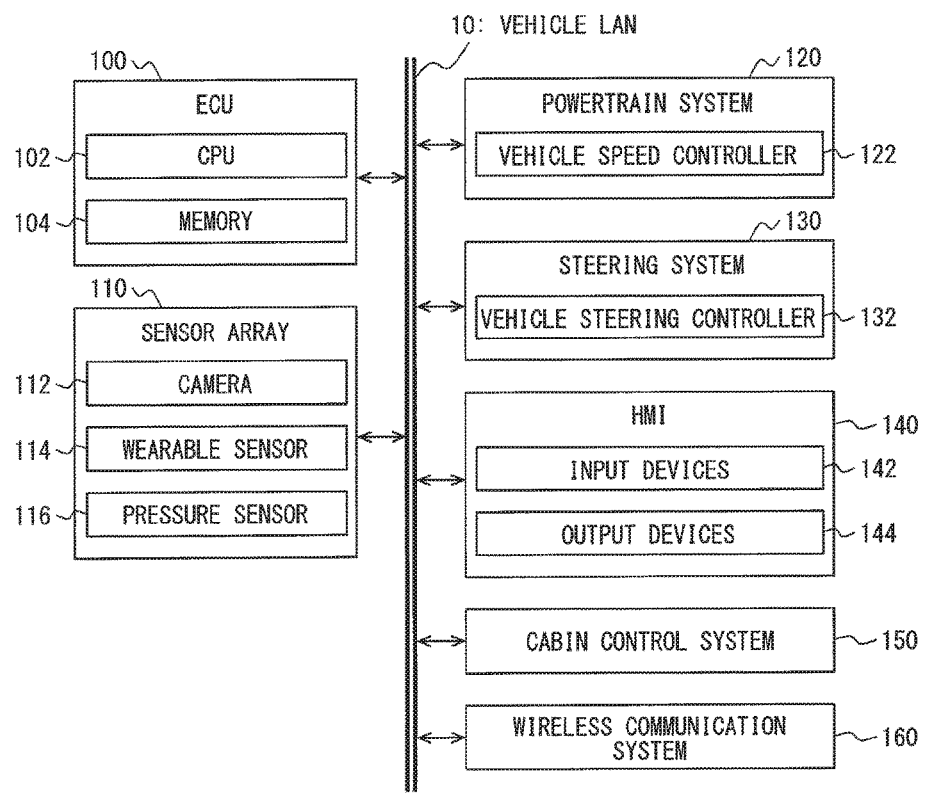
FIG. 2 is a system view of a vehicle LAN.

The subject vehicle 1 includes a variety of on-board systems as shown in FIG. 2. Here, FIG. 2 is a system diagram, in which a vehicle local-area network (LAN) 10 serves as a network bus which interconnects an electronic control unit (ECU) 100, a sensor array 110, a powertrain system 120, a steering system 130, a human-machine interface (HMI) 140, a cabin control system 150, and a wireless communication system 160.

The ECU 100 is a processor which includes a central processing unit (CPU) 102 and a memory 104. The CPU 102 is preferably a microcomputer or microprocessor. The memory 104 is preferably a semiconductor memory such as random access memory (RAM), read only memory (ROM), flash memory, of a combination of these. The memory 104 has stored thereon instructions which program the CPU 102 to perform a variety of tasks as will be described later. In an alternative embodiment, the ECU 100 may be implemented as an off-board remote processor, such as through the use of a remote cloud computing server which communicates with the subject vehicle 1 via the wireless communication system 160. The ECU 100 serves as a vehicle controller which controls the subject vehicle 1. The ECU 100 and the subject vehicle 1 together form a vehicle system that provides lane change assistance as will be described below.

The sensor array 110 is a group of feature sensors configured to detect features of a passenger. In the present embodiment, the sensor array 110 preferably includes a camera 112, a wearable sensor 114, and a pressure sensor 116. Each of these sensors may be physically mounted in different locations of the subject vehicle 1, or may be provided separately from the vehicle 1 as will be described below. In addition, as shown in FIG. 2, the sensor array 110 is coupled to the ECU 100 through the vehicle LAN 10. In an alternative embodiment, the sensor array 110 may be directly connected to the ECU 100.

The powertrain system 120 controls the powertrain of the subject vehicle 1. For example, the powertrain system 120 may control the acceleration, deceleration, and braking of the subject vehicle 1. The powertrain system 120 includes a vehicle speed controller 122 which interfaces with external devices. In the present embodiment, the vehicle speed controller 122 receives command signals from the ECU 100, and controls the speed of the subject vehicle 1 in accordance with those command signals. In FIG. 2, the vehicle speed controller 122 is coupled to the ECU 100 through the vehicle LAN 10. In an alternative embodiment, the vehicle speed controller 122 may be directly connected to the ECU 100.

The steering system 130 controls the steering (i.e., the heading) of the subject vehicle 1 by controlling at least one of the wheels 2 of the subject vehicle 1. The steering system 130 includes a vehicle steering controller 132 which interfaces with external devices. In the present embodiment, the vehicle steering controller 132 receives command signals from the ECU 100, and controls the heading of the subject vehicle 1 in accordance with those command signals. In FIG. 2, the vehicle steering controller 132 is coupled to the ECU 100 through the vehicle LAN 10. In an alternative embodiment, the vehicle steering controller 132 may be directly connected to the ECU 100.

The HMI 140 allows a passenger to input information to the subject vehicle 1, and allows the passenger to receive information about the subject vehicle 1. The HMI 140 includes a plurality of input devices 142 and a plurality of output devices 144. The input devices 142 include, but are not limited to, a keyboard, a keypad, a touch screen, a voice input channel, as well as wired and wireless protocols for receiving passenger input from another device. For example, the input devices 142 may include a short range wireless transceiver which receives passenger input from a mobile device operated by the passenger. The output devices 144 include, but are not limited to, a display for visual output, a speaker for audio output, tactile feedback elements (e.g., embedded in a steering wheel or seat), as well as the above mentioned wired and wireless protocols, which may be used to output data to a mobile device operated by a passenger.

The cabin control system 150 controls various miscellaneous aspects of the subject vehicle 1, such as door locking and lighting. The wireless communication system 160 allows the subject vehicle 1 to communicate with other vehicles as well as infrastructure. The wireless communication system 160 may allow communication over a wide variety of protocols such as cellular, short range wireless, and so on.

While the system diagram of FIG. 2 shows each of the ECU 100, the sensor array 110, the powertrain system 120, the steering system 130, the HMI 140, the cabin control system 150, and the wireless communication system 160 as separate systems, this is not intended to limit the physical relationships between these systems. For example, each of the vehicle speed controller 122 and the vehicle steering controller 132 may be implemented as part of the ECU 100. In other words, while FIG. 2 shows a system layout, this does not limit the physical layout of the network. Additionally, while FIG. 2 shows the use of the vehicle LAN 10, this is merely illustrative and not intended to be limiting. Each of the system components in FIG. 2 may be directly connected to each other instead.

Next, each of the sensors in the sensor array 110 will be described.

The camera 112 is preferably an optical camera mounted to face a passenger of the vehicle 1. The term "passenger" as used herein may refer to a passenger in any seat of the vehicle 1, including the driver seat. The camera 112 may be, for example, mounted within the dashboard panel of the vehicle 1 to capture raw optical data of the passenger's face. In the present embodiment, the camera 112 is configured to detect visual features of the passenger including at least one of an expression and a pupil diameter of the passenger. Here, the expression of the passenger may be broadly categorized as one of "comfortable" and "uncomfortable", or may be more specifically categorized into a plurality of expression types such as "happy", "calm", "anxious", or "scared".

It should be noted that while the camera 112 is described as detecting the expression and pupil diameter of the passenger, this description is not intended to limit the camera 112 as performing the signal processing that analyzes the raw optical data (i.e., of the passenger's face) to determine the expression or pupil diameter of the passenger. Instead, for example, the camera 112 may simply capture and send raw optical data to the ECU 100, in which case the ECU 100 performs the signal processing required to determine the expression and pupil diameter of the passenger. Further alternatively, the camera 112 may send the raw optical data to a remote processor or remote server for full or partial processing at a remote location.

The wearable sensor 114 is preferably worn by the passenger to detect bio features of the passenger. For example, the wearable sensor 114 may be a wrist-mounted sensor worn on the wrist of the passenger. In the present embodiment, the wearable sensor 114 detects at least one of a pulse rate, a body temperature, and a perspiration rate of the passenger. As with the camera 112, the wearable sensor 114 may perform the signal processing required to determine the pulse rate, the body temperature, and the perspiration rate of the passenger, or the wearable sensor 114 may send raw data to the ECU 100 or another processor for remote processing.

FIG. 2 illustrates an example where the wearable sensor 114 directly interfaces with the vehicle LAN 10, e.g., through a physical cable. However, in the present embodiment, the wearable sensor 114 may also be physically separate from the vehicle 1, such that communication between the wearable sensor 114 and the vehicle LAN 10 is performed wirelessly, e.g., through the input devices 142 or the wireless communication system 160. For example, the wearable sensor 114 may be an off-the-shelf, commercial fitness sensor. In other words, while the system diagram in FIG. 2 depicts the wearable sensor 114 as part of the sensor array 110, the wearable sensor 114 is not necessarily physically tied to the vehicle LAN 10.

The pressure sensor 116 is preferable mounted on the steering wheel of the vehicle 1 to detect a pressure applied by the passenger on the steering wheel. As an alternative or in addition to being mounted on the steering wheel, the pressure sensor 116 may be mounted on portions of vehicle which are typically gripped by a passenger, such as handles.

In the present embodiment, the ECU 100 is programmed to perform an assisted lane change control process which accounts for the comfort of passengers. Here, "assisted lane change" refers to a semi-autonomous or fully-autonomous (i.e., automatic) lane change which is performed by the vehicle 1. The degree to which the lane change is performed autonomously is not intended to be limited. For example, "assisted lane change" is intended to include a lane change which is initiated by a passenger (e.g., through the actuation of a turn signal) and executed by the vehicle 1. Further, "assisted lane change" is also intended to include a lane change which is both initiated and executed by the vehicle 1.

In the present embodiment, the ECU 100 executes assisted lane changes based on a plurality of lane change parameters which define the characteristics of the assisted lane changes. These lane change parameters may be stored in the memory 104, or alternatively may be stored in a remote server. In particular, in the present embodiment, the lane change parameters include at least one of a maximum speed, maximum acceleration, maximum yaw angle, and minimum inter-vehicle distance. The maximum speed indicates that maximum speed that the vehicle 1 may reach during the execution of the assisted lane change. Similarly, the maximum acceleration indicates the maximum acceleration that the vehicle 1 may reach during the execution of the assisted lane change. The maximum yaw angle indicates the maximum degree to which the heading of the vehicle 1 may deviation from straight ahead, i.e., how much the vehicle 1 may turn during the execution of the assisted lane change. Finally, the minimum inter-vehicle distance indicates a minimum distance that must exist between the vehicle 1 and other vehicle in the target lane of the assisted lane change.

Typically, such lane change parameters are predetermined, e.g., by a manufacturer of the vehicle 1, based on extensive study and experimentation to ensure safe and efficient assisted lane changes. However, the present inventors recognized that even if an assisted lane change is objectively safe by safety standards, the assisted lane change may not feel safe to a passenger who, for example, may not be familiar with automated driving technology. For instance, a passenger may prefer that an assisted lane change be performed with lower acceleration levels as compared to a manually executed lane change. As a result, simply using predetermined lane change parameters to perform every assisted lane change may not sufficiently account for the comfort of each passenger.

Figure 3:
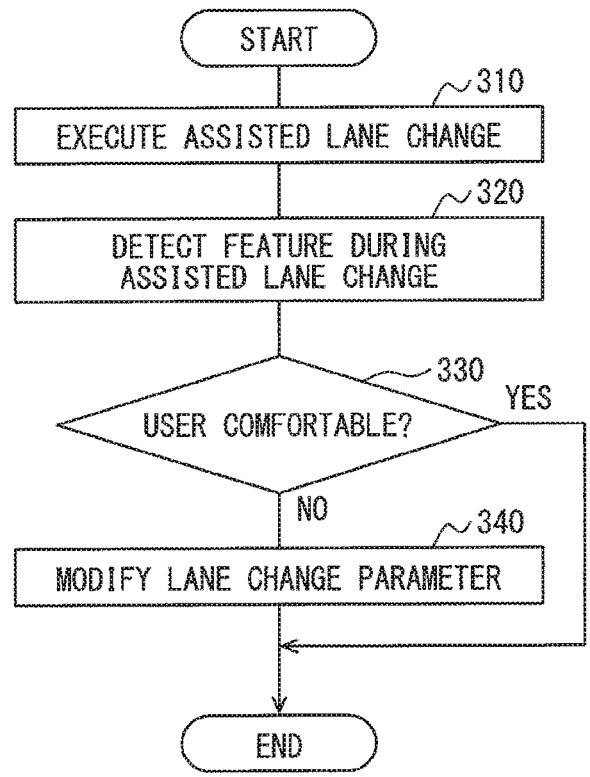
FIG. 3 is a flow chart depicting a control process.

In view of the above, in the present embodiment, the ECU 100 is configured to perform a control process shown in FIG. 3.

At step 310, the ECU 100 executes an assisted lane change based on lane change parameters which may be, for example, stored on the memory 104. It should be noted that "execute" in this context is not intended to limit the ECU 100 as the sole controller responsible for performing the assisted lane change. Instead, the ECU 100 may cooperate with other controllers to execute the assisted lane change. For example, at step 310, the ECU 100 may simply instruct a separate autonomous driving ECU (not illustrated) to perform the assisted lane change.

Next, at step 320, at least one feature of a passenger is detected. Specifically, the ECU 100 communicates with at least one of the sensors in the sensor array 110 to detect a corresponding feature of the passenger. In the present embodiment, the ECU 100 preferably communicates with each of the camera 112, the wearable sensor 114, and the pressure sensor 116 to detect all of the above described features of the passenger. However, this is not limiting. For example, not all features of the passenger may be detectable at all times. If the passenger is not facing directly at the camera, the pupil diameter of the passenger may not be sufficiently visible to the camera 112. As another example, the passenger may not be wearing the wearable sensor 114. Accordingly, the present embodiment is not limited to detecting any specific feature of the passenger; rather, at least one detected feature of the passenger is received by the ECU 100 from the sensor array 110.

Next, at step 330, the ECU 100 determines whether the passenger was comfortable during the assisted lane change based on the one or more features of the passenger detected during that assisted lane change. In the present embodiment, the ECU 100 preferably uses a machine learning model for classifying the one or more detected features into either "comfortable" or "uncomfortable". Specifically, the one or more detected features of the passenger from step 320 is preferably used as the inputs to a machine learning model, which then outputs one of "comfortable" and "uncomfortable" based on these inputs.

The specific machine learning model is not intended to be limited. As an example, a simple decision tree model may be used. In this example, a decision tree may first consider the expression of the passenger. If the expression of the passenger is "uncomfortable" or "scared", the decision tree may immediately output a determination of "uncomfortable". Conversely, if the expression of the passenger is "comfortable" or "calm", or if the expression of the passenger is unknown, the decision tree may proceed to consider further features of the passenger such as pulse rate. Alternatively, more complex models such as a neural network or a complex decision tree model (e.g., random forest) may be used. In the present embodiment, the machine learning model used at step 330 is preferably pre-trained, e.g., by the manufacturer of the vehicle 1.

If the ECU 100 determines at step 330 that the passenger is comfortable ("YES" at step 330), the process terminates.

Conversely, if the ECU 100 determines at step 330 that the passenger is uncomfortable ("NO" at step 330), the process continues to step 340.

At step 340, the ECU 100 modifies the lane change parameters that determine the characteristics of the assisted lane change such that the subsequent assisted lane change will be less likely to make the passenger uncomfortable, i.e., modify the lane change parameters to be less aggressive. In particular, the ECU 100 may modify any one or more of the maximum speed, maximum acceleration, maximum yaw angle, and minimum inter-vehicle distance mentioned previously. For example, the ECU 100 may reduce the values of the maximum speed, maximum acceleration, and maximum yaw angle, or increase the minimum inter-vehicle distance.

The present embodiment is not limited to any specific method of modifying the lane change parameters. For example, the ECU 100 may randomly modify one lane change parameter to be less aggressive, or the ECU 100 may modify more than one lane parameter at a time. The modified lane change parameters are stored by the ECU 100 in, e.g., the memory 104, and the modified lane change parameters are used during the next iteration of the control process shown in FIG. 3. By repeating the control process of FIG. 3, the ECU 100 eventually arrives at a combination of lane change parameters that results in a comfortable assisted lane change for the passenger.

In the present embodiment, the memory 104 may store a plurality of sets of lane change parameters which are specific to different passenger profiles. This is because, for example, a household may have several different passengers for a particular vehicle 1. In this case, each passenger may have different preferences for an assisted lane change should be executed. In this case, when a particular passenger enters the vehicle 1, that passenger may select their own passenger profile to use a corresponding set of lane change parameters.

As a result of performing the exemplary control process illustrated in FIG. 3, the ECU 100 is able to modify the lane change parameters based on the comfort of the passenger in order to improve the comfort level of subsequent assisted lane changes.

Second Embodiment

A second embodiment of the present disclosure will be explained with reference to FIGS. 4 and 5.

Figure 4:
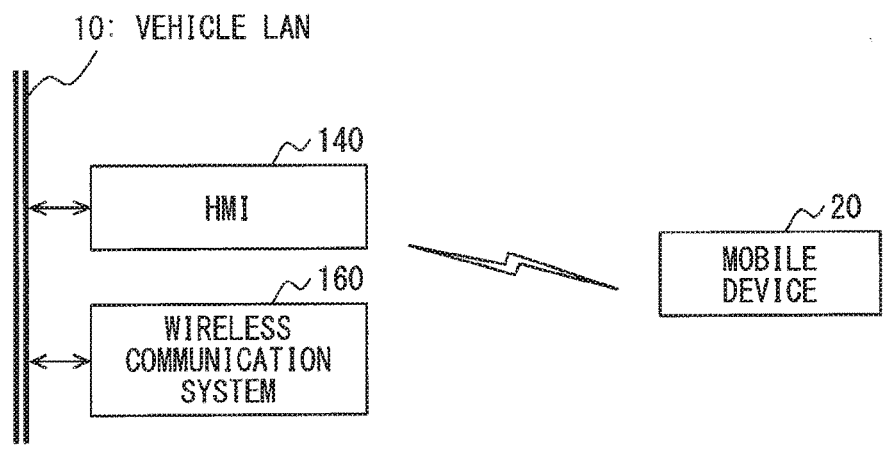
FIG. 4 is a system view of a vehicle LAN and a mobile device.

In the present embodiment, as shown in FIG. 4, the vehicle LAN 10 is configured to communicate with a mobile device 20 through the HMI 140 or the wireless communication system 160. The mobile device 20 may be, for example, a smartphone or a smartwatch carried by a passenger.

The mobile device 20 is configured to store mobile parameters which are lane change parameters specific to the owner of the mobile device 20. In the present embodiment, the vehicle 1 is configured to automatically sync with the mobile device 20 when the vehicle 1 is turned on. Specifically, the ECU 100 automatically detects whether the mobile device 20 is in range, and if so, the ECU 100 downloads the mobile parameters to use as the lane change parameters during assisted lane changes. For example, the ECU 100 may store the downloaded mobile parameters in the memory 104 to overwrite the existing lane change parameters. Alternatively, the passenger may manually send the mobile parameters from the mobile device 20 to the ECU 100.

If a plurality of mobile devices 20 are within range (e.g., if multiple passengers are in the vehicle 1, with each passenger having their own mobile device 20), the ECU 100 preferably downloads the least aggressive set of lane change parameters to use as the lane change parameters during assisted lane changes. By using the least aggressive (i.e., most comfortable) set of lane change parameters, the ECU 100 may ensure that all passengers are comfortable during assisted lane changes.

Figure 5:
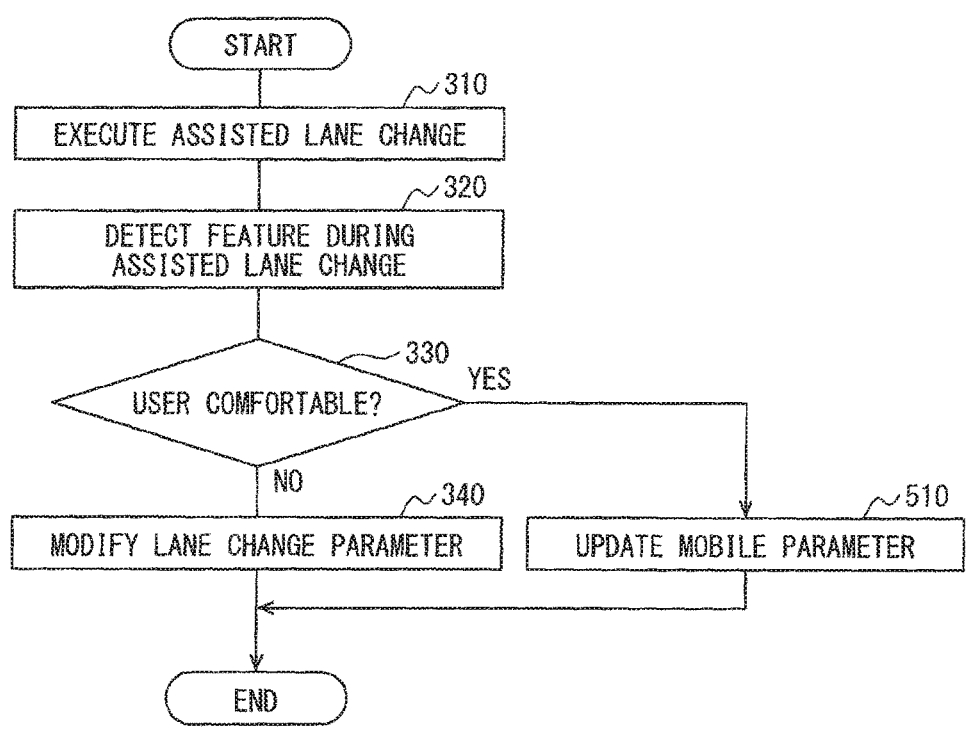
FIG. 5 is a flow chart depicting a control process.

In the present embodiment, the ECU 100 is configured to perform the control process shown in FIG. 5. Here, steps 310 to 340 correspond to those described in the previous embodiment, and therefore overlapping descriptions are omitted here for brevity.

In FIG. 5, it is assumed that the ECU 100 has downloaded and stored the mobile parameters from the mobile device 20 as the lane change parameters at an earlier time (not illustrated), such as when ignition is turned on. However, although the ECU 100 is using the mobile parameters of the passenger, the actual preferences of the passenger may still change over time. For example, a passenger may be sick, and therefore prefer less aggressive lane changes than those described by the mobile parameters. Accordingly, in the present embodiment as well, the ECU 100 also perform steps 310 to 340 to continuously modify the lane change parameters if the passenger is determined as being uncomfortable during any assisted lane change. In other words, the ECU 100 initially downloads the mobile parameters from the mobile device 20 (e.g., when ignition is turned on) and stores the mobile parameters as the lane change parameters. Thereafter, the ECU 100 modifies the lane change parameters as appropriate in a manner similar to the first embodiment.

In addition, in the present embodiment, if the ECU 100 determines that the passenger is comfortable ("YES" at step 330), instead of terminating the process, the ECU 100 continues to step 510. At step 510, the ECU 100 updates the mobile parameters stored on the mobile device 20 with the current lane change parameters used by the ECU 100. In other words, when the ECU 100 modifies the lane change parameters, the ECU 100 also modifies the mobile parameters of the mobile device 20 in a corresponding manner. As a result, the ECU 100 ensures that the mobile parameters in the mobile device 20 are always up to date.

In the present embodiment, lane change parameters are portable as mobile parameters using the mobile device 20, and therefore a passenger may "carry" their preferred lane change parameters to different vehicles. Moreover, through the control process shown in FIG. 5, the mobile parameters stored in the mobile device 20 may be updated by the ECU 100.

Third Embodiment

A third embodiment of the present disclosure will be explained with reference to FIG. 6.

In the above described embodiments, an example was provided in which the ECU 100 uses a pre-trained machine learning model for determining whether the passenger is comfortable or uncomfortable during an assisted lane change. However, in the present embodiment, the ECU 100 is further configured to train this machine learning model, i.e., by performing online training.

Figure 6:
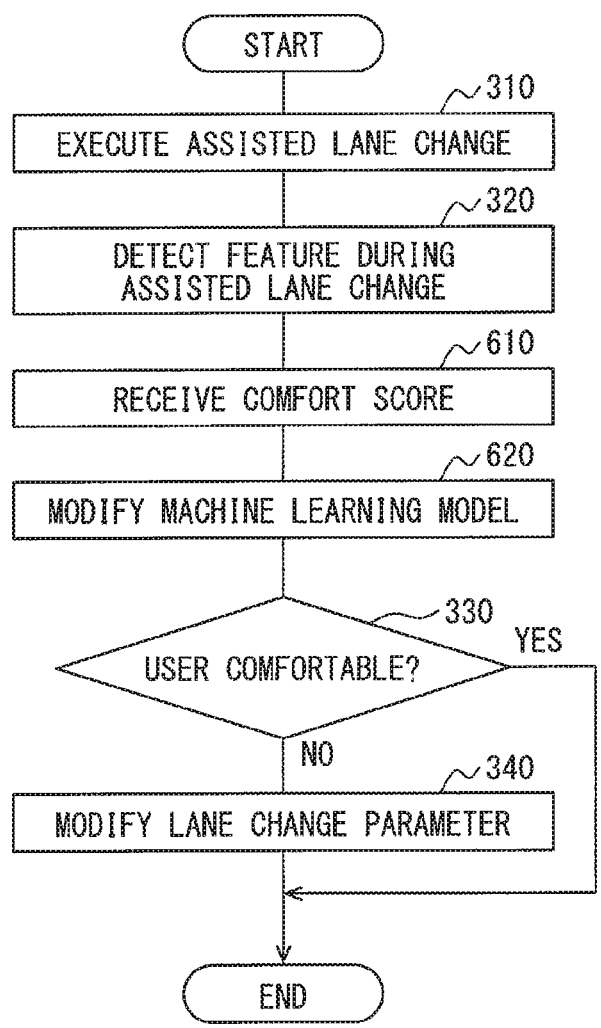
FIG. 6 is a flow chart depicting a control process.

In FIG. 6, steps 310 to 340 correspond to those described in the previous embodiments, and therefore overlapping descriptions are omitted here for brevity. In the present embodiment, after step 320, the ECU 100 proceeds to step 610 and asks the passenger to determine whether the assisted lane change (performed at step 310) was comfortable or uncomfortable. Specifically, the ECU 100 preferably outputs this question to the passenger through the output devices 144 of the HMI 140, and receives a comfort score from the passenger through the input devices 142 of the HMI 140. The score from the passenger may be a simple yes/no (i.e., "comfortable" or "uncomfortable"), or may be a more specific score such as ranging from one ("least comfortable") to ten ("most comfortable").

After receiving the score from the passenger, the ECU 100 continues to step 620 and uses the score to train the machine learning model for determining whether the passenger was comfortable during the assisted lane change. Specifically, the ECU 100 uses the score as a desired output of the machine learning model. For example, if the passenger described the assisted lane change as being comfortable, then the machine learning model should also output "comfortable" based on the detected features of the passenger. Well known methods of training machine learning models may be used here. For example, if a neural network is used as the machine learning model, a difference between the score from the passenger and the output of the neural network may be used as an error value for backpropagation. As another example, if a decision tree model such as random forest is used as the machine learning model, the score from the passenger and the features of the passenger detected during that same assisted lane change may be added to a training data set for building the decision tree model.

In the present embodiment, at step 330, the ECU 100 may directly use the score from the passenger instead of using the machine learning model to determine whether the passenger was comfortable during the assisted lane change. In other words, for example if the passenger entered a score corresponding to "comfortable" at step 610, the ECU 100 may automatically determine that the passenger was comfortable during the assisted lane change.

The control process of the present embodiment is preferably combined with those of the previous embodiments such that the machine learning model is only trained during certain periods. For example, the training process of the present embodiment may be performed for a certain number of assisted lane changes to train the machine learning model, and then the trained machine learning model may be used according to the control processes of the previous embodiments.

Other Embodiments

The present disclosure is described with reference to the above embodiments, but these embodiments are not intended to be limiting. A variety of modifications which do not depart from the gist of the present disclosure are contemplated.

In the above described embodiments, the features of the passenger are detected during the assisted lane change. However, the ECU 100 may also detect features of the passenger while not executing an assisted lane change, in order to establish a baseline of comfort for the passenger. In other words, the ECU 100 may compare the features of the passenger during normal driving to the features of the passenger during an assisted lane change to more accurately determine whether the passenger is uncomfortable during the assisted lane change.

In the above described embodiments, the lane change parameters are modified when the ECU 100 determines that the passenger is uncomfortable during an assisted lane change. However, the ECU 100 may also modify the lane change parameters when determining that the passenger is comfortable during an assisted lane change. For example, as a passenger becomes familiar with assisted lane changes, the lane change parameters may be modified to be more aggressive (e.g., higher maximum speed, or lower minimum inter-vehicle distance) to return to factory-determined levels. In this case, if the ECU 100 determines that the passenger is comfortable, and the current lane change parameters are less aggressive than factory-determined levels, the ECU 100 may modify the lane change parameters to be more aggressive.

In an alternate embodiment, when the ECU 100 determines that the passenger was uncomfortable during an assisted lane change, the ECU 100 may prompt the passenger to identify which aspect of the assisted lane change was uncomfortable, e.g., whether maximum speed, maximum acceleration, maximum yaw angle, or inter-vehicle distance was the primary uncomfortable aspect. In this regard, the ECU 100 may modify the most relevant lane change parameter based on the answer from the passenger.

The above embodiments are described with respect to a wearable sensor 114 and a mobile device 20. In an alternative embodiment, the wearable sensor 114 may be implemented as part of the mobile device 20. For example, if the mobile device 20 is a smartwatch, the wearable sensor 114 may be sensors mounted in the smartwatch.

Any processing functions by the ECU 100 described above may be, partially or in full, processed by a remote processor, and transmitted to the vehicle 1 through the wireless communication system 160.

The present disclosure includes implementation as a vehicle controller, which is a processor that includes a CPU and a memory. The vehicle controller is programmed to execute the control processes described with respect to the above described embodiments.

The invention claimed is:

1. A vehicle system, comprising:
a processor coupled to a vehicle, the processor configured to store a lane change parameter; and
a feature sensor that detects a feature of a passenger in the vehicle, wherein
the processor is programmed to
control the vehicle to execute an assisted lane change based on the lane change parameter, the lane change parameter defining a characteristic of the assisted lane change,
communicate with the feature sensor to detect the feature of the passenger during the assisted lane change,
determine whether the passenger was comfortable during the assisted lane change based on the detected feature of the passenger, and
modify the lane change parameter upon determining that the passenger was uncomfortable, wherein
the processor uses a machine learning model to determine whether the passenger was comfortable during the assisted lane change,
the vehicle system further comprises a human-machine interface mounted in the vehicle, and
the processor is programmed to
receive a comfort rating for the assisted lane change from the passenger through the human-machine interface, and
train the machine learning model based on the detected feature and the received comfort rating.

2. The vehicle system of claim 1, further comprising:
a mobile device that stores a mobile parameter corresponding to the passenger, wherein
the processor is programmed to
download the mobile parameter from the mobile device upon detecting that the mobile device is in the vehicle, and
store the downloaded mobile parameter as the lane change parameter.

3. The vehicle system of claim 2, wherein
the processor is programmed to, when modifying the lane change parameter, modify the mobile parameter stored in the mobile device in a corresponding manner.

4. The vehicle system of claim 2, wherein
the mobile device includes the feature sensor.

5. The vehicle system of claim 1, wherein
the machine learning model is one of a neural network and a decision tree model.

6. The vehicle system of claim 1, wherein
the feature sensor includes one or more of:
a camera mounted in the vehicle, the camera detecting at least one of an expression of the passenger and a pupil diameter of the passenger as the feature of the passenger,
a wearable sensor worn the passenger, the wearable sensor detecting at least one of a pulse, a body temperature, and a perspiration rate of the passenger as the feature of the passenger, and
a pressure sensor mounted on a steering wheel of the vehicle, the pressure sensor detecting a pressure applied by the passenger as the feature of the passenger.

7. The vehicle system of claim 1, wherein
the lane change parameter includes at least one of a maximum speed, a maximum acceleration, a maximum yaw angle, and a minimum inter-vehicle distance.

8. The vehicle system of claim 7, wherein
the processor is programmed to, when modifying the lane change parameter, perform at least one of:
decreasing the maximum speed,
decreasing the maximum acceleration,
decreasing the maximum yaw angle, and
increasing the minimum inter-vehicle distance.

9. A vehicle controller, comprising:
a central processing unit (CPU) coupled to a vehicle and in communication with a feature sensor that detects a feature of a passenger in the vehicle; and
a memory coupled to the CPU, the memory configured to store a lane change parameter, wherein
the CPU is programmed to
communicate with the feature sensor to detect the feature of the passenger during an assisted lane change, the lane change parameter defining a characteristic of the assisted lane change,
determine whether the passenger was comfortable during the assisted lane change based on the detected feature of the passenger, and
modify the lane change parameter upon determining that the passenger was uncomfortable, wherein
the CPU uses a machine learning model stored in the memory to determine whether the passenger was comfortable during the assisted lane change,
a human-machine interface is mounted in the vehicle, and
the CPU is programmed to
receive a comfort rating for the assisted lane change from the passenger through the human-machine interface, and
train the machine learning model based on the detected feature and the received comfort rating.

10. The vehicle controller of claim 9, wherein
the CPU is in communication with a mobile device that stores a mobile parameter corresponding to the passenger, and
the CPU is programmed to
  download the mobile parameter from the mobile device upon detecting that the mobile device is in the vehicle, and
  store the downloaded mobile parameter in the memory as the lane change parameter.

11. The vehicle controller of claim 10, wherein
the CPU is programmed to, when modifying the lane change parameter, modify the mobile parameter stored in the mobile device in a corresponding manner.

12. The vehicle controller of claim 10, wherein
the mobile device includes the feature sensor.

13. The vehicle controller of claim 9, wherein
the machine learning model is one of a neural network and a decision tree model.

14. The vehicle controller of claim 9, wherein
the CPU is in communication with, as the feature sensor, one or more of:
  a camera mounted in the vehicle, the camera detecting at least one of an expression of the passenger and a pupil diameter of the passenger as the feature of the passenger,
  a wearable sensor worn the passenger, the wearable sensor detecting at least one of a pulse, a body temperature, and a perspiration rate of the passenger as the feature of the passenger, and
  a pressure sensor mounted on a steering wheel of the vehicle, the pressure sensor detecting a pressure as the feature of the passenger.

15. The vehicle controller of claim 9, wherein
the lane change parameter includes at least one of a maximum speed, a maximum acceleration, a maximum yaw angle, and a minimum inter-vehicle distance.

16. The vehicle controller of claim 15, wherein
the CPU is programmed to, when modifying the lane change parameter, perform at least one of:
  decreasing the maximum speed,
  decreasing the maximum acceleration,
  decreasing the maximum yaw angle, and
  increasing the minimum inter-vehicle distance.

* * * * *